US 6,746,682 B2

(12) United States Patent
Daffunchio et al.

(10) Patent No.: US 6,746,682 B2
(45) Date of Patent: Jun. 8, 2004

(54) BIOLOGICAL CONTROL OF HORN FLIES

(76) Inventors: Julio Angel Daffunchio, Rivadavia 762, 1744 Moreno, Provincia de Buenos Aires (AR); Eduardo Abel Palazzo, Alsina 81—O'Higgins, 6748 Partido de Chacabuco, Provincia de Buenos Aires (AR)

(*) Notice: Subject to any disclaimer, the term of this patent is extended or adjusted under 35 U.S.C. 154(b) by 0 days.

(21) Appl. No.: 09/964,077

(22) Filed: Sep. 26, 2001

(65) Prior Publication Data

US 2003/0056427 A1 Mar. 27, 2003

(51) Int. Cl.[7] .................... A01K 51/00; A01N 25/00
(52) U.S. Cl. ........................... 424/405; 449/1
(58) Field of Search .............. 435/3, 283.1; 424/405

(56) References Cited

U.S. PATENT DOCUMENTS 3,911,121 A * 10/1975 Roberts .............. 424/219

OTHER PUBLICATIONS

Alston, Genral concepts of biolog. control, Apr. 1996, AG/IPM/04, pp. 1–7.*

Core, Jim, Attacking flies with wasps, Aug. 2002, Agricultural Res. Magazine, pp. 1–4.*

* cited by examiner

Primary Examiner—Mike Wityskyn
Assistant Examiner—Deborah K. Ware
(74) Attorney, Agent, or Firm—Greer, Burns & Crain, Ltd.

(57) ABSTRACT

A method is provided for the biocontrol of horn fly for protecting livestock. The method includes defining an area for managing the livestock and placing a number of wasp's hives containing wasps of the species *Polybia scutellaris*, in an effective amount to control the flies. A honey containing food for the wasps is placed in an area at a distance from the hives.

17 Claims, No Drawings

BIOLOGICAL CONTROL OF HORN FLIES

BACKGROUND OF THE INVENTION

1. Field of the Invention

The present invention relates to the biocontrol of pests and more particularly refers to a method for controlling flies and, more specifically the invention refers to the biocontrol of flies of the species *Haematobia irritans*, horn fly, by managing wasps, preferably of the species *Polybia scutellaris*, in an area with a population of such flies. The managing of wasps generally comprises the installation of honeycomb or hives containing wasps.

To the purpose of the present specification the terms honeycomb device must be understood, unless otherwise indicated, as comprising wasps's honeycomb, wasp's hives or any other container, house or device providing the necessary conditions, as natural as possible, for the housing and living of the desired wasps.

While the present specification will make reference to the horn flies as the preferred insect for the biocontrol, the invention must be understood as applied to any kind of undesired flies.

2. Description of the Prior Art

It is well known to control pests through biocontrol, that is by using a pest predator for controlling the pest development by killing the pest, for example. Biocontrol seeks to attain a balance between a pest insect and its natural enemies, thereby reducing or eliminating the need for chemical control.

Among the several pests, the fly is an undesired insect either for human beings as well as for some animals such as the livestock, such as the cattle, which is particularly attacked by the horn fly. Horn fly occurs from Canada to Argentina in the Western Hemisphere, and Europe to North Africa in the other Hemisphere. Horn flies and stable flies were introduced from Europe, presumably along with cattle at the time of early settlement. Horn flies do not bite man but are almost exclusively associated with cattle and sometimes with horses and game elk. They spend almost their entire adult lives on and among the hair of their hosts, females leaving for only a few minutes to oviposit. They can feed whenever they wish, which they do often to the distress of cattle.

Horn fly larvae develop only in fresh cow dung. In hot weather horn flies develop rapidly, completing a generation every 3 weeks or so at 30° C., or monthly at 25° C. The young larvae, which cannot survive desiccation, live at the moist surface of the dung; older larvae live within tunnels made in drier dung by beetle larvae. Pupation takes place in the soil under the dung or nearby. Larvae are yellow-white maggots about 2–12 mm long. These are cylindrical in cross section, and taper from the rear to the head. Pupae are reddish-brown and 3–4 mm long.

Adult horn flies average 5 mm long and are about ½ to ⅔ the size of a typical house fly. They are charcoal gray in color with two dark stripes on the thorax and a few diffuse spots on the top of abdomen. The mouthparts are visibly extended forwards from the head as a piercing proboscis and the palps are longer than ½ the length of the proboscis.

Congregating on those areas of the body where they are not likely to be disturbed (base of horns, neck, throat, belly, thighs, back etc.), horn flies suck blood from livestock through their needle-like mouthparts. Such feeding causes weight loss, reduced milk production, and reduced vitality. Furthermore, animals become so annoyed that they may injure themselves while attempting to dislodge the flies. Infestations of 4,000 to 10,000 flies per animal are common in some parts of the countries. It has been calculated that a cattle herd infested with horn flies has a weight loss of about 10% to 15% for pasture bovines, a weight loss of about 7% to 8% for weaning calves and the looses of milk production is about 10% to 20% in a milk cow.

On finding a host, horn flies remain on it and others in the same herd for life, moving to different anatomical sites for regulating their temperature and minimizing exposure to the wind. Both horn fly sexes suck blood, males feeding approximately 20 times and female approximately 40 times daily.

Favored by warm, moist weather, horn flies emerge in spring and seek out host animals. Although they locate hosts successfully during the day, they usually disperse at night, sometimes traveling as far as 5 miles.

During the spring and summer months, a new brood of flies emerges 5 to 7 days later and repeats the cycle. As winter approaches, newly formed pupae overwinter giving rise to a new generation of flies the following spring. Although most prevalent in spring and summer, horn flies continue to produce a new generation approximately every 2 weeks well into autumn.

Insecticidal control options for horn flies include whole-animal sprays, self-applicating devices, feed-through insecticides and growth regulators, and controlled-release devices, such as ear tags and tapes. Not all products are effective against horn flies, and some products cannot be used on lactating dairy cattle.

Whole-animal sprays provided rapid relief from fly pressure. Animal sprays are applied either as a dilute coarse spray, often applied under high pressure to soak the skin, or as a fine low-volume, more concentrated mist.

Self-applicating devices include back rubber covered with an absorbent material treated with an insecticide-oil solution, or dust bags filled with an insecticidal dust. Back rubbers and dustbags should be placed in gateways, near water and feed source, and in other areas where animals will make frequent contact with them.

Feed-throughs include insecticidal feed additives, treated mineral blocks, and bolus formulations. Unless the farm was very isolated or participating in an area-wide management program, feed-throughs may not provide satisfactory fly suppression.

Controlled-release ear tags and tapes are generally very effective for horn fly control in certain farm areas.

Pour-on treatments involves the application of an insecticide along the backline of the animal at a prescribed dosage of topical products.

The topical products that are currently approved for control and available fit into three major categories: Organophosphates (OP's), pyrethroid and endectocides.

In Argentina sprays and pour-ons are generally used to control horn flies. Dairy cattle are treated more frequently than beef cattle. The increased treatment frequencies against horn fly populations may be one of the factors responsible for the development of pyrethroid resistance. It is known that if a horn fly population develops resistance to one synthetic pyrethroid it is resistant to all of them. Once established, resistance will persist for a number of years.

When resistance of insecticide is established the use should be stopped. Cattle should be treated before and at the end of fly season by another class of insecticide to reduce the number of resistant flies that will produce overwintering generation. The ability to alternate between insecticide classes may be limited due to the type of cattle or compatibility of the treatment method with the herd management system.

The use of organophosphated compounds is prohibited in many countries as long as it causes important risks for the human health and ecosystem. Continued use of chemical insecticides over a long period of time has resulted in public concerns of the possible risk of chemical residues in meat and milk.

It is known that horn flies are attacked by a number of parasites and predators in the manure pats. Unfortunately, practical means of utilizing this natural control has not been successful. Producers, therefore, rely on chemical means of protecting their cattle from horn flies. The use of alternate methods of pest control such as the application of biological control agents is desirable to minimize the use of insecticides.

In recent years, commercial insectaries have reared and sold fly parasites as wasps which deposit eggs on fly pupae. The wasp larvae feed on the developing fly and kill it. Release of wasps has provided effective fly control in some poultry houses but this is ineffective as a control of pasture fly pests such as face fly and horn fly.

The success of such biological control depends, however, upon the use of (a) a control agent for a target harmful pest, (b) proper timing of application of the control agent, and (c) precise depositing of control agents in contact with the harmful pests and predators.

Current methods of control are only partially effective and the available chemicals are highly toxic. Hence there is a clear need for more effective, more persistent and less toxic methods of fly control.

SUMMARY OF THE INVENTION

It is therefore one object of the present invention to provide a method for the biocontrol of horn fly for protecting livestock, the method comprising defining an area for managing the livestock and placing a number of wasp's hives containing wasps of the species *Polybia scutellaris*, in an effective amount to control the flies, and placing a honey containing food for the wasps in an area at a distance from the hives.

It is still another object of the present invention to provide a method for the biocontrol of flies, the method comprising:

i. defining a target fly activity area;

ii. determining the approximate population density of the fly in the area;

iii. placing a number of honeycomb devices containing a number of wasps, wherein each honeycomb-like device defines a wasp activity area, wherein the number of devices is calculated in relation to the extension of the fly activity area and the extension of the wasp activity area whereby the extension of the fly activity area is covered by the extension of the wasp activity area; and iv. placing a food compound that is attractive of the wasps within each wasp activity area.

It is a further object of the present invention to provide a method for the biocontrol of target flies selected from the group comprising *Haematobia irritans* (horn fly), *Musca domestica L.* (house fly), *M. autumnales* (face fly) and *Stomoxys calcitrans (L.)* (stable fly), the target fly being preferably the *Haematobia irritans* (horn fly), the method comprising:

i. defining a target fly activity area with inhabitants such as human livings and/or animals selected from the group comprising cattle, equine, pigs and any breeding animal, and more preferably the area is a cattle breeding herd, or a corral, or a cattle feed lot, a dairy farm, diary installation, etc., ii. determining the approximate population density of the fly in the area;

iii. placing, preferably in the shade or in the shadow of at least one tree, a number of honeycomb devices, such as natural wasp's honeycombs or hives, containing a number of wasps, with each honeycomb-like device defining a wasp activity area, wherein the natural wasp's honeycomb or wasp's hive may be obtained by cutting a portion of tree containing a natural wasp hive and bringing the tree portion containing the hive into the target fly activity area and fixing the tree portion in a desired location, wherein the number of devices is calculated in relation to the extension of the fly activity area and the extension of the wasp activity area whereby the extension of the fly activity area is covered by the extension of the wasp activity area, with a number of from about 1 to about 25 animals per wasps honeycomb device in an area from about 5 to about 100 hectares for a cattle breeding herd, or a number of from about 1 to about 20 animals per honeycomb device in an area from about 1 to about 2 hectares for a feed lot, or a number of from about 1 to about 20 animals per wasps honeycomb device in an area from about 1 to about 2 hectares for a diary farm; with the wasps selected from the sub-order Apocrytae, preferably wasps of the species *Polybia scutellaris*, with each honeycomb device being preferably placed at a height of at least 2 meters from the ground and at about 50 meters from any site selected from the group comprising a water tank, basin, pool, pond, cattle watering place, cattle feeding place, for cattle breeding herds and feed lots, and iv. placing a food compound that is attractive of the wasps within each wasp activity area, the food compound being preferably a honey-containing food placed at a distance between 1 to 10 cm from each honeycomb device and in an amount between 100 to 200 grams per honeycomb device, with the food compound being most preferably honey placed at a distance of 5 cm from each honeycomb device.

It is even a further object of the present invention to provide a biological control system for controlling a fly selected from the group comprising *Haematobia irritans* (horn fly), *Musca domestica L.* (house fly), *M. autumnales* (face fly) and *Stomoxys calcitrans (L.)* (stable fly), the system comprising:

at least one wasp's hive device placed in a selected site of an area inhabited by the fly, wherein the hive contains a number of wasps that are effective to control the fly, with the hive being allocated at a height from the ground effective to prevent the hive from being contacted by any mammalian inhabiting the area, and at least one honey-containing food compound that is attractive to the wasps, the food compound being placed at a distance from the hive effective to keep the wasps living in a desired wasps activity area.

It is still a further object of the present invention to provide a method for the biocontrol of flies, the method comprising placing a number of wasp's hive devices containing wasp in a fly activity area, and placing a food compound that is attractive of the wasps, the food compound being placed at a distance from each hive device effective to keep the wasps living in a desired wasps activity area for controlling the fly.

The above and other objects, features and advantages of this invention will be better understood when taken in connection with the accompanying description.

DESCRIPTION OF THE PREFERRED EMBODIMENTS

As stated above, while the use of parasitic wasps have been already proposed in the art to control house flies and stable flies, these proposal have not reached a stage beyond the experimental one, without practical results being shown in the practical field. This has been due to the difficulties in managing the wasps, in other words it has not been possible to provide a stable wasp population and the experiments show positive results only by releasing wasps in a field without any control.

The inventors have created and developed an new system and method for biologically controlling the fly, most particularly the horn fly, dramatically reducing the number of horn flies in the back of the animals inhabiting an area with horn flies, namely a fly activity area. The number of horn flies in the back of bovine and equine herds was reduced to a value that is considered below a threshold corresponding to economic looses. In effect, the number of flies was reduced to only 20–30 flies per animal without the need of treating the animals with insecticides, or alternatively, with low doses. The method of the present invention provides a control of the horn fly in an efficient manner, also eliminating the need of using insecticides or other chemicals that would negatively affect the ecosystem and the human beings.

The method of the present invention basically comprises the placing of honeycomb or hive devices, such as natural honeycomb or hives, containing wasps, preferably wasps of the sub-order Apocrytae, and most preferably wasps of the species *Polybia scutellaris*, in a ratio, for a breeding cattle herd, of at least from 1/25 honeycomb or hive device/animals in an area of from about 5 to about 100 hectares.

In any event, it will be apparent to any person skilled in the art that the optimum ratio between the number of hive devices and the number of animals will depend from, among other parameters, the wasp species, the extension of the breeding area, the species and population of the fly to be controlled. In a preferred embodiment, the fly species is *Haematobia irritans* commonly known as horn fly.

While specific reference has been made to the application of the invention to a breeding cattle herd, the invention is well applicable to any other field wherein the inhabitants thereof, either human beings, cattle, mammalians, etc., must be protected from the flies. For example, the inventive method and system are applicable to feed lots with a number of honeycomb devices containing wasps, preferably wasps of the sub-order Apocrytae, and most preferably wasps of the species *Polybia scutellaris*, in a ratio of at least 1–20 animals/device, in an extension of about 2 hectares, or the extension that is appropriate for a desired feed lot.

The invention can also be applied to a diary farm or diary installation, by placing wasps hives containing wasps, preferably wasps of the sub-order Apocrytae, and most preferably wasps of the species *Polybia scutellaris*. The ratio devices/animals may also depend from the number of animals that is managed for each milking.

Preferably, in all the applications each device contains from about 4,000 to about 6,000 wasps and the devices are located at a height from about 2 meters to about 3 meters, protected or sheltered from the direct sun rays and from the wind. For example, the hive or honeycomb devices are placed in the shadow of trees, in the same trees, under a roof, roofing, shed, cover, etc. It is important to keep the honeycombs and hives sheltered from the sun and wind in order to have the same habitat conditions required by the wasps. Additionally, because the infested animals like to stay in the shade during the high temperature months, which is the time of most activity for the flies, particularly the horn flies, the hive is near the flies.

It is also necessary to provide a watering source close to the honeycombs and hives, such as water troughs, drinking dishes or watering places for the animals.

The inventors have found that the wasps of the species *Polybia scutellaris* efficiently work as a biological control for the horn fly dramatically reducing the number of flies per animal as compared to the number of flies in the animals treated with conventional insecticides, that is 20–30 flies per animal with the invention, vs. 300–400 flies per animal, with insecticides.

It is possible that the traditional use and experiments attempted with wasps for controlling the horn flies had failed because of the behavior characteristics, adaptation to the environment, biology, presence of food, and interaction of other species with the parasitic wasps. The utilization of wasps of the species *Polybia scutellaris* seems to be a key point in the method of biological control of the invention.

In addition, another important aspect related to the success of the biological control according to the invention is maintaining a high population or density of wasps in an area that naturally has insufficient food for the wasps. In natural conditions, the wasp's honeycombs or hives containing wasps of the species *Polybia scutellaris* are spaced apart from each other by large extensions, what would cause the hives to be non useful for the desired control activity, with each natural located panel covering an area of 10,000 $m^2$. The inventors have managed the hive devices and food compounds in a manner to have a high wasp population in a small area, the food compound being artificially prepared with commercial bees honey.

The process of artificial feeding comprises the steps of placing small containers containing from about 100 grams to about 200 grams of bee honey, each container being placed at a distance of about 5 cm. to the entrance to each hive device, this food supplement permitting the complete feeding of the entire high population of wasps. The amount of food compound for each hive mainly depends from the weather conditions. For example, during cold weather, with temperatures between 5° C. and 15° C., approximately 100 grams of honey is used for each hive or honeycomb. The food container must be constantly controlled in order to refill the same each time the containers are empty or about to be empty. When the room temperature is 20° C. or above 20° C. the quantity of honey and the refilling frequency will depend from the natural food that is available in the wasp activity area.

It will be apparent to any skilled person in the art that if natural pastures are available in or close to the breeding cattle herds, feed lots and dairy farms, the provision of artificial food may be regulated or even eliminated, particularly in the springtime and summer time.

The method of the invention is useful in several cattle farms, preferably in intensive breeding farms, wherein the herds may be bovine y/or equine; or in any micro agricultural cattle breeding system; the method providing a reduction in the amount of horn flies to a number of flies per animal that is below a threshold over which the number of flies causes economical looses.

The method of the invention was successfully employed in several agricultural farms for more than a year, wherein each animal was maintained with a number of flies as low as 20 to 30 flies during the period with high room temperatures, which is the time of most activity of the horn fly. It is important to remark that the honeycomb or hive devices can be, according to the invention, maintained for years and that the number of such devices may be increased if the number of animals is increased into the herd or the number of flies naturally increases. It is also possible to replace the hives by new ones if the old ones have been damaged or the same are abandoned by their inhabitants. The hive or honeycomb devices may be naturally obtained by cutting a portion of a tree branch containing a wasp's hive or can be manufactured with all the necessary means to provide the living conditions required by the desired wasps.

The invention is further illustrated by means of the following Examples which is meant to be an illustration only and is not intended to limit the present invention to these specific embodiments.

EXAMPLE 1

Management of Honeycomb Devices

A number of natural wasp's hives have been obtained in winter because the activity of the wasps in this time is low. The hives were obtained by cutting such branches of trees having a hive, leaving a portion of 5 cm. of branch at each side of the wasp's hive or honeycomb. In all the cases, for obtaining such branch portions containing hives fixed thereon, the personnel used protection systems and clothing usually employed in the apiculture.

EXAMPLE 2

Arrangement of the Hives for Biological Control of Horn Fly in a Breeding Cattle Herd The test was carried out in Province of Buenos Aires, Republic of Argentina, in a 200 hectares farm with cattle and agriculture.

100 cows were allocated in two (2) lots, 50 cows per lot, with collecting gangways for directing the cows to an area with trees, the lots and the forest area was defined as the target fly activity area. Four hive devices containing *Polybia scutellaris* wasps were installed in the trees at a height of 2 meters from the ground. The fly population was approximately determined in a number of between about 200 and 300 flies per animal.

At 10 days from the step of placing the hive devices the number of horn flies per animal was evaluated by counting the flies animal by animal. The control was periodically carried out and the number of flies per animal remained between about 30 and about 40 for a year period.

EXAMPLE 3

Arrangement of the Hives for Biological Control of Horn Fly in a Feed Lot System The test was carried out in Province of Buenos Aires, Republic of Argentina, in a 200 hectares farm with cattle and agriculture.

80 calves were allocated in 1 hectare lot, defined as the target fly activity area, with a rumination and resting area of 1 hectare. In a small group of trees, four hive devices containing *Polybia scutellaris* wasps were installed at a height of 3 meters from the ground. The average fly population was approximately determined in a number of between about 200 and 300 flies per animal.

At 10 days from the step of placing the hive devices the number of horn flies per animal was evaluated by counting the flies animal by animal. The control was periodically carried out and the number of flies per animal remained between about 30 and about 40 for a year period.

EXAMPLE 4

Arrangement of the Hives for Biological Control of Horn Fly in a Diary Establishment The establishment comprised 150 animals of which 50 animals were under milk production. Five hive devices containing *Polybia scutellaris* wasps were installed in the group of trees at a height of 2 meters from the ground and at a distance of 50 meters from watering places and ponds.

In the diary milking installations a number of 2 hive devices at a height of 3 meters were installed. The average fly population was approximately determined in a number of between about 200 and 300 flies per animal.

At 10 days from the step of placing the hive devices the number of horn flies per animal was evaluated by counting the flies animal by animal. The control was periodically carried out and the number of flies per animal remained between about 30 and about 40 for a year period.

EXAMPLE 5

Arrangement of the Hives for Biological Control of Horn Fly in an Equine Herd Four horses were allocated in a lot of 5 hectares, defined as the target fly activity area. In a group of trees within the lot, 2 hive devices containing *Polybia scutellaris* wasps were installed at a height of 3 meters from the ground. The average fly population was approximately determined in a number of between about 15 and 20 flies per animal.

At 10 days from the step of placing the hive devices the number of horn flies per animal was evaluated by counting the flies animal by animal. The control was periodically carried out and the number of flies per animal remained about 4 for a year period.

EXAMPLE 6

Method of Artificial Feeding

In all the above tests (examples 2–5) a pvc container was placed at a distance of 5 cm from the entrance to each of the hive devices, and the containers were periodically refilled with 100 grams of bees honey.

While preferred embodiments of the present invention have been illustrated and described, it will be obvious to those skilled in the art that various changes and modifications may be made therein without departing from the scope of the invention as defined in the appended claims.

We claim:

1. A method for biocontrol of horn flies of the species (*Haematobia irritans*), the method comprising:
   i. defining a target horn fly activity area;
   ii. determining an approximate population density of said horn flies in the area;
   iii. placing a number of honeycomb devices containing a number of *Polybia scutellaris* wasps, wherein each honeycomb device defines a wasp activity area, wherein the number of honeycomb devices is calculated in relation to an extension of the target horn fly activity area and an extension of the wasp activity area whereby the extension of the target horn fly activity area is covered by the extension of the wasp activity area; and iv. placing a food compound that is attractive to said wasps within each said wasp activity area.

2. The method of claim 1, wherein the target horn fly activity area comprises a cattle breeding herd and the step of placing the honeycomb devices containing a number of said wasps comprises placing one honeycomb device per about 1 to about 25 animals and wherein the target horn fly activity area extends from about 5 to about 100 hectares.

3. The method of claim 2, wherein the honeycomb devices containing said wasps are arranged at a height of at least 2 meters from the ground.

4. The method of claim 2, wherein the honeycomb devices containing said wasps are arranged at about 50 meters from a place selected from the group consisting of a water tank, a basin, a pool, a pond, a cattle watering place, and a cattle feeding place.

5. The method of claim 2, wherein the honeycomb devices containing said wasps are arranged in a shaded area.

6. The method of claim 2, wherein the honeycomb devices containing said wasps are arranged at a shadow of trees, fixed in at least one tree.

7. The method of claim 1, wherein the target horn fly activity area is cattle feed lot and said step of placing the honeycomb devices containing a number of said wasps comprises placing one honeycomb device per about 1 to about 20 animals, and wherein the target horn fly activity area extends from about 1 to about 2 hectares.

8. The method of claim 7, wherein the honeycomb devices containing said wasps are arranged at a height of at least 2 meters from the ground.

9. The method of claim 7, wherein the honeycomb devices containing said wasps are arranged at about 50 meters from a place selected from the group consisting essentially of a water tank, a basin, a pool, a pond, a cattle watering place, and a cattle feeding place.

10. The method of claim 7, wherein the honeycomb devices containing said wasps are arranged in a shaded area.

11. The method of claim 7, wherein the honeycomb devices containing said wasps are arranged at a shadow to trees, fixed in at least one tree.

12. A method of claim 1, wherein the target horn fly activity area comprises a dairy farm and the step of placing the honeycomb devices containing a number of said wasps comprises placing one honeycomb device per about 1 to about 20 animals, and wherein the target horn fly activity area extends from about 1 to about 2 hectares.

13. The method of claim 12, wherein the honeycomb devices containing said wasps are arranged at a height of at least 2 meters from the ground.

14. The method of claim 12, wherein the honeycomb devices containing said wasps are arranged to about 50 meters from a place selected from the group consisting essentially of a water tank, a basin, a pool, a cattle watering place, and a cattle feeding place.

15. The method of claim 12, wherein the honeycomb devices containing said wasps are arranged in a shaded area.

16. The method of claim 12, wherein the honeycomb devices containing said wasps are arranged at a shadow of trees, fixed in at least one tree.

17. The method of claim 1, wherein the food compound is a honey-containing food in an amount between 100 to 200 grams per honeycomb device and said food compound is placed at a distance between 1 to 10 cm from each of the honeycomb devices.

* * * * *